United States Patent
Ramirez, Jr. et al.

(10) Patent No.: US 10,180,180 B2
(45) Date of Patent: Jan. 15, 2019

(54) GEAR MOTOR PUMP ASSEMBLY

(71) Applicant: MEDELA HOLDING AG, Baar (CH)

(72) Inventors: Emilio A. Ramirez, Jr., Roselle, IL (US); David Cho, Arlington Heights, IL (US); Sarah Loeffel, Genoa, IL (US)

(73) Assignee: MEDELA HOLDING AG, Baar (CH)

( * ) Notice: Subject to any disclaimer, the term of this patent is extended or adjusted under 35 U.S.C. 154(b) by 350 days.

(21) Appl. No.: 14/496,437

(22) Filed: Sep. 25, 2014

(65) Prior Publication Data

US 2015/0082925 A1 Mar. 26, 2015

Related U.S. Application Data

(60) Provisional application No. 61/882,329, filed on Sep. 25, 2013.

(51) Int. Cl.
| | |
|---|---|
| *F16H 25/12* | (2006.01) |
| *F04B 9/02* | (2006.01) |
| *F04B 9/04* | (2006.01) |
| *F04B 17/03* | (2006.01) |
| *A61M 1/06* | (2006.01) |

(52) U.S. Cl.
CPC ............... *F16H 25/12* (2013.01); *A61M 1/06* (2013.01); *A61M 1/062* (2014.02); *F04B 9/02* (2013.01); *F04B 9/047* (2013.01); *F04B 17/03* (2013.01); *Y10T 74/18568* (2015.01); *Y10T 74/18576* (2015.01)

(58) Field of Classification Search
CPC .. F16H 25/12; A61M 1/06; F04B 9/02; F04B 9/047; F04B 17/03
See application file for complete search history.

(56) References Cited

U.S. PATENT DOCUMENTS

| | | | | | |
|---|---|---|---|---|---|
| 2,536,396 | A | * | 1/1951 | Scheibler | F16H 33/02 192/61 |
| 2,625,030 | A | * | 1/1953 | Wooster | D06F 33/00 417/319 |
| 2,988,189 | A | * | 6/1961 | Thomas | F16D 23/12 192/40 |
| 4,365,962 | A | * | 12/1982 | Regelsberger | B25D 16/003 173/104 |
| 4,428,398 | A | * | 1/1984 | Mito | F16K 17/06 137/530 |
| 4,779,031 | A | | 10/1988 | Arends et al. | |
| 4,931,679 | A | | 6/1990 | Fournier | |
| 5,038,088 | A | | 8/1991 | Arends et al. | |
| 5,090,513 | A | * | 2/1992 | Bussinger | B60K 28/04 180/271 |

(Continued)

FOREIGN PATENT DOCUMENTS

GB 2070349 A 9/1981

*Primary Examiner* — Zakaria Elahmadi
(74) *Attorney, Agent, or Firm* — Marshall, Gerstein & Borun LLP

(57) ABSTRACT

A compact gear motor pump assembly is disclosed. The gear motor pump assembly includes a motor driving a gear train and an output shaft in a first direction and a second direction, creating a pumping action. The present gear motor pump assembly offers an efficient and quiet operation through incorporation of springs within the assembly. The present assembly is designed for use with devices, specifically medical devices requiring a pumping action, for example, breast pumps.

12 Claims, 5 Drawing Sheets

(56) References Cited

U.S. PATENT DOCUMENTS

| | | | |
|---|---|---|---|
| 5,749,737 A | 5/1998 | Zuin | |
| 5,942,819 A | 8/1999 | Burgess et al. | |
| 6,145,396 A * | 11/2000 | Ko | F16H 25/20 74/89.23 |
| 6,927,513 B2 * | 8/2005 | Schreier | F16H 25/20 310/12.01 |
| 7,259,487 B2 * | 8/2007 | Mullin | H02K 3/524 310/216.023 |
| 7,412,906 B2 * | 8/2008 | Ponziani | B62D 5/0406 180/443 |
| 7,549,847 B1 * | 6/2009 | McClatchey | F04B 9/02 417/15 |
| 7,755,240 B2 | 7/2010 | Yang et al. | |
| 7,939,978 B2 | 5/2011 | Best et al. | |
| 8,181,546 B2 * | 5/2012 | Larsen | F16D 11/14 192/69 |
| 8,314,522 B2 | 11/2012 | Bena et al. | |
| 8,662,263 B2 * | 3/2014 | Deutloff | B60T 7/107 188/162 |
| 9,630,307 B2 * | 4/2017 | Ludy | B25D 11/04 |
| 9,682,330 B1 * | 6/2017 | Sherry | B01D 1/30 |
| 9,765,870 B1 * | 9/2017 | Fox | F16H 39/02 |
| 9,874,428 B1 * | 1/2018 | Nelson | G01B 3/1005 |
| 2004/0093969 A1 * | 5/2004 | Nielsen | A47C 20/041 74/89.23 |
| 2005/0013708 A1 * | 1/2005 | Peeler | B01L 3/0206 417/415 |
| 2006/0021457 A1 * | 2/2006 | Jacobs | F16H 19/001 74/352 |
| 2007/0025866 A1 * | 2/2007 | Douyama | F04B 17/03 417/423.3 |
| 2008/0006105 A1 * | 1/2008 | Ko | A63B 22/02 74/89.23 |
| 2008/0030161 A1 | 2/2008 | Ludwig et al. | |
| 2008/0291650 A1 | 11/2008 | Hautvast et al. | |
| 2009/0124111 A1 | 5/2009 | Rabotti | |
| 2010/0139429 A1 * | 6/2010 | Ku | B66F 3/08 74/89.37 |
| 2010/0162837 A1 * | 7/2010 | Cavalier | F16H 25/22 74/89.23 |
| 2010/0242642 A1 * | 9/2010 | Ganter | F16H 25/20 74/89.23 |
| 2012/0307476 A1 | 12/2012 | Masuzawa et al. | |
| 2013/0056316 A1 * | 3/2013 | Sano | B60T 13/746 188/2 D |
| 2013/0292215 A1 * | 11/2013 | Eguchi | F16H 25/2266 188/72.1 |
| 2013/0305857 A1 * | 11/2013 | Heeg | B60N 2/0224 74/89.23 |
| 2014/0054057 A1 * | 2/2014 | Ludy | B25D 11/12 173/48 |
| 2014/0209344 A1 | 7/2014 | Kalayjian et al. | |
| 2014/0326089 A1 * | 11/2014 | Wu | F16H 25/20 74/89.23 |
| 2014/0338480 A1 * | 11/2014 | Wu | F16H 25/20 74/89.23 |
| 2015/0194857 A1 | 7/2015 | Hernandez et al. | |
| 2015/0377329 A1 * | 12/2015 | Wu | F16H 25/20 74/89.38 |
| 2016/0033024 A1 * | 2/2016 | Yulkowski | F16H 47/02 49/335 |

\* cited by examiner

GEAR MOTOR PUMP ASSEMBLY

TECHNICAL FIELD

The present disclosure relates to gear motor pump assembly. Specifically, the present disclosure relates to a compact gear motor pump assembly providing quiet, efficient operation for use in a variety of applications requiring a pumping action, including medical devices.

BACKGROUND

Compact medical pumps are highly portable, which reduces the need to limit their use to a clinical setting for many medical treatments. For example, administering a drug using a pump instead of a number of injections spaced apart in time results in a more consistent treatment, which is often more effective and therefore cost effective as well. Additionally, a compact medical pumping apparatus, potentially sized so that it can be concealed in the clothes of a patient, and is capable of pumping fluids from a remote reservoir to the patient, would also be advantageous.

Another type of compact medical pump is a breast pump. Breast pumps are well known devices for extracting milk from a breast of a user. A breast pump may be used if the baby or infant is not itself able to express milk from the breast, or if the mother is separated from the baby or infant, for example, if away from the baby at work. Portable breast pumps are particularly useful for working mothers. One complaint from users is that the breast pumps are noisy. Therefore portable breast pumps, which are quiet, discreet and efficient, are key features particularly when the user is in a semi-public setting.

Regardless of the specified use, a medical pump apparatus would benefit from a gear motor pump assembly having a compact configuration. A compact gear motor pump assembly may be useful in any number of devices, such as medical devices requiring a pumping action. Additionally, because traditional gear motor pumps tend to create a noise or knocking sound during operation, it would also be advantageous to provide a gear motor pump assembly having quiet, smooth and efficient operation. Providing a compact gear motor pump assembly using an acme thread shaft and a helical gear in all stages helps in the overall smooth, quiet and discreet operation. Accordingly, the present disclosure provides these and other advantages.

SUMMARY

The present disclosure provides a gear motor pump assembly, and more particularly, a compact gear motor pump assembly with a motor driving a gear train and an output shaft in a back and forth motion or direction, creating a pumping action. The present assembly is designed for use with devices, specifically medical devices requiring a pumping action, for example, breast pumps.

In an embodiment of the invention, a gear motor pump assembly is disclosed. The gear motor pump assembly comprises a housing defining a gear chamber and having a cover, a motor having a motor shaft extending axially therefrom, the motor connected to the housing, a gear train positioned inside the gear chamber and connected to the motor, an output shaft engaging with and movable by the gear train, at least one compression spring positioned between one of the gear chamber and the cover and the gear train, and wherein when the motor is energized, the gear train rotates in a first direction moving the output shaft a first distance, and wherein the gear train rotates in a second direction opposite to the first direction moving the output shaft in a second distance opposite the first distance, creating a pumping motion.

In an embodiment, the gear train comprises a pinion gear, a first stage gear and a last stage gear. The last stage gear is an output gear having a central hub for engaging the output shaft.

In an embodiment, the compression spring includes a helical spring.

In an embodiment, the compression spring includes an O-ring.

In an embodiment, the assembly includes two compression springs, disposed on either side of the central hub of the output gear.

In another embodiment, a first compression spring is disposed between the output gear and the housing cover and a second compression spring is disposed between the output gear and the gear box.

In another embodiment, the first and second compression springs provide a cushion between the output gear and the housing cover and the gear box.

In yet another embodiment, a gear motor pump assembly for use in a pumping device is disclosed. The gear motor pump assembly comprises a housing defining a gearbox and having a cover, a motor having a motor shaft extending axially therefrom, the motor connected to the housing, a gear train including an output gear having a central hub positioned within the gear chamber and connected to the motor, an output shaft engaging with and moveable by the gear train, at least two springs installed one on either side of the output gear central hub, wherein the spring absorbs concussion between the output gear, the gear box and the cover as the output gear moves back and forth axially along the shaft, and wherein, when the motor is energized in a first stage, the gear train rotates in a first direction moving the output shaft a first distance, and wherein when the motor is energized in a second stage, the gear train rotates in a second direction opposite to the first direction moving the output shaft in a second distance opposite the first distance, wherein the movement of the output shaft between the first distance and the second distance creates a pumping motion.

It is therefore an advantage and objective of the present disclosure to provide a gear motor pump assembly having quiet operation.

It is also an advantage and objective of the present disclosure to provide a gear motor pump assembly with smooth, efficient operation.

It is also an advantage and objective of the present disclosure to provide a gear motor pump assembly with long lasting, reliable operation.

It is also an advantage and objective of the present disclosure to provide a gear motor assembly for use within a medical device.

It is also an advantage and objective of the present disclosure to provide a gear motor pump assembly for use in a medical pumping device.

Additional features and advantages of the present invention are described in, and will be apparent from, the detailed description of the presently preferred embodiments and from the drawings.

BRIEF DESCRIPTION OF THE DRAWINGS

The drawing figures depict one or more implementations in accord with the present concepts, by way of example only.

DETAILED DESCRIPTION

Figure 1:
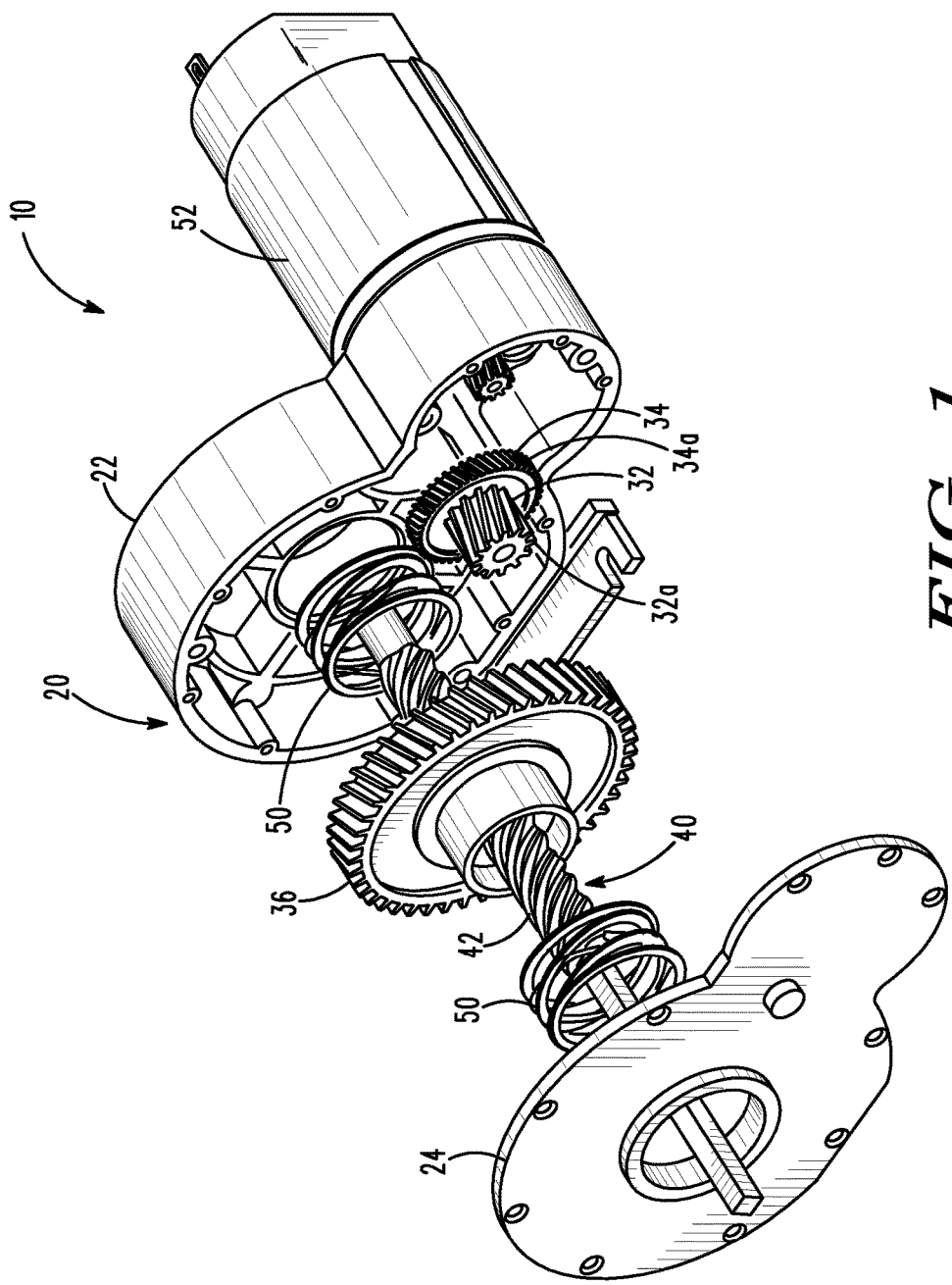
FIG. 1 is an exploded perspective view of an embodiment of a gear motor pump assembly.
Figure 2:
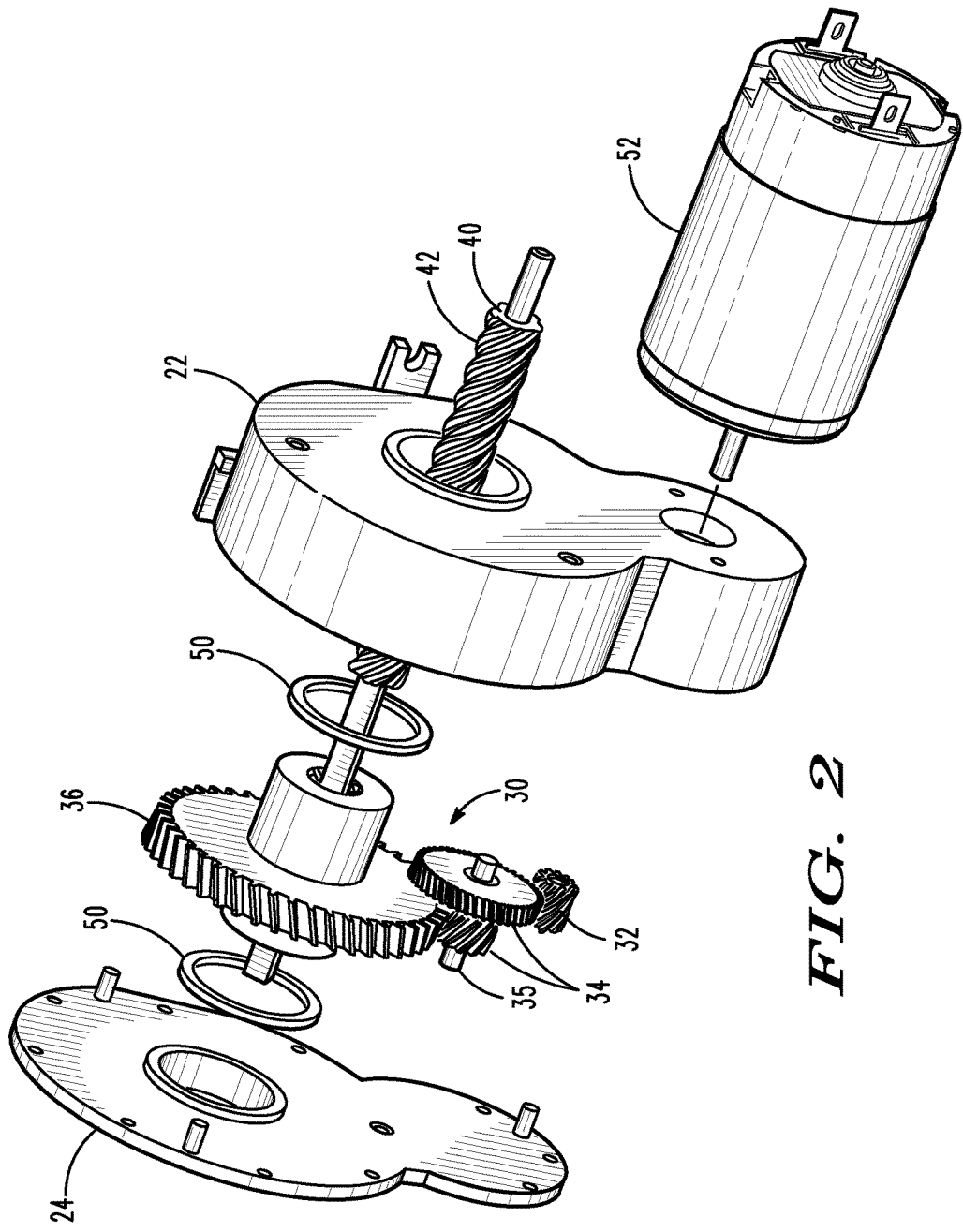
FIG. 2 is an exploded perspective view of an embodiment of the gear motor pump assembly
Figure 3:
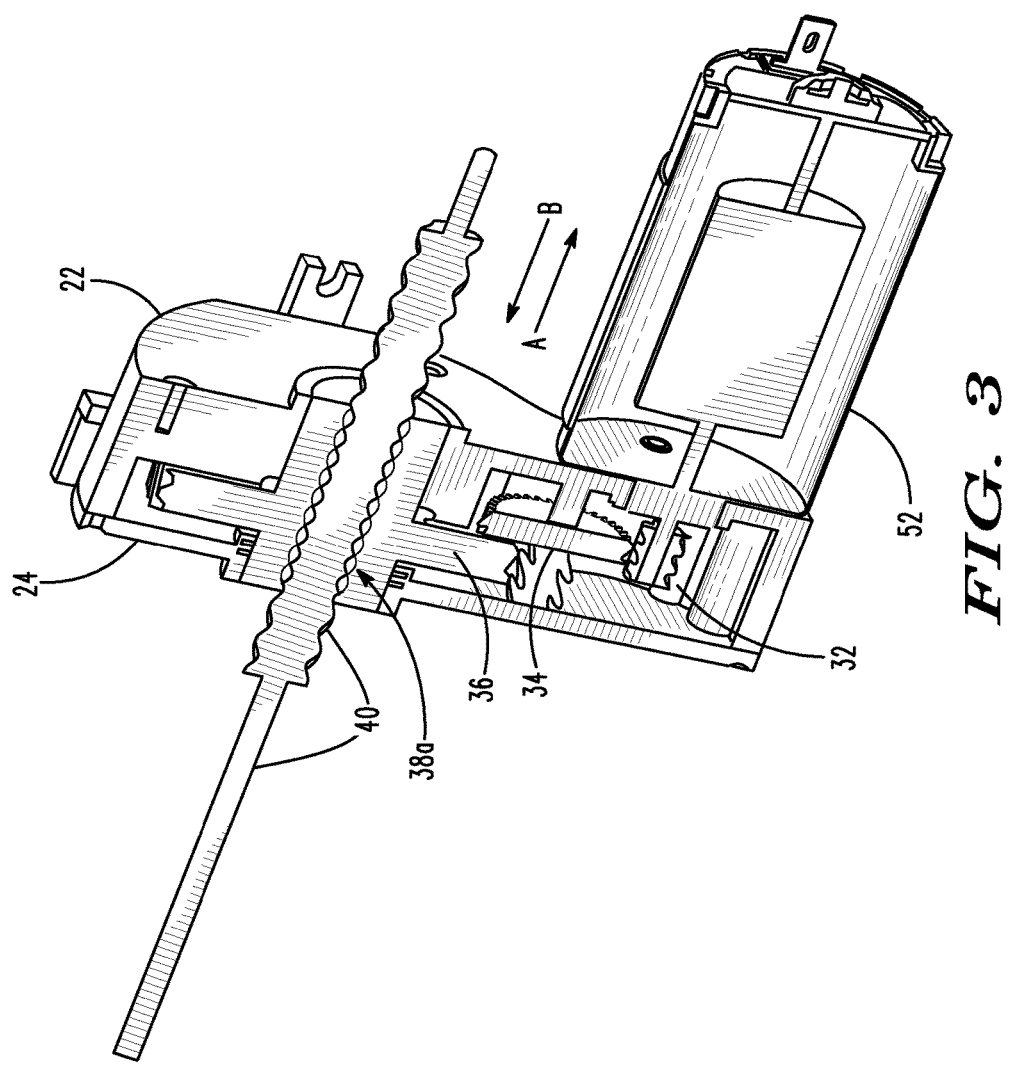
FIG. 3 is an cross sectional view of an assembled gear motor pump assembly.
Figure 4:
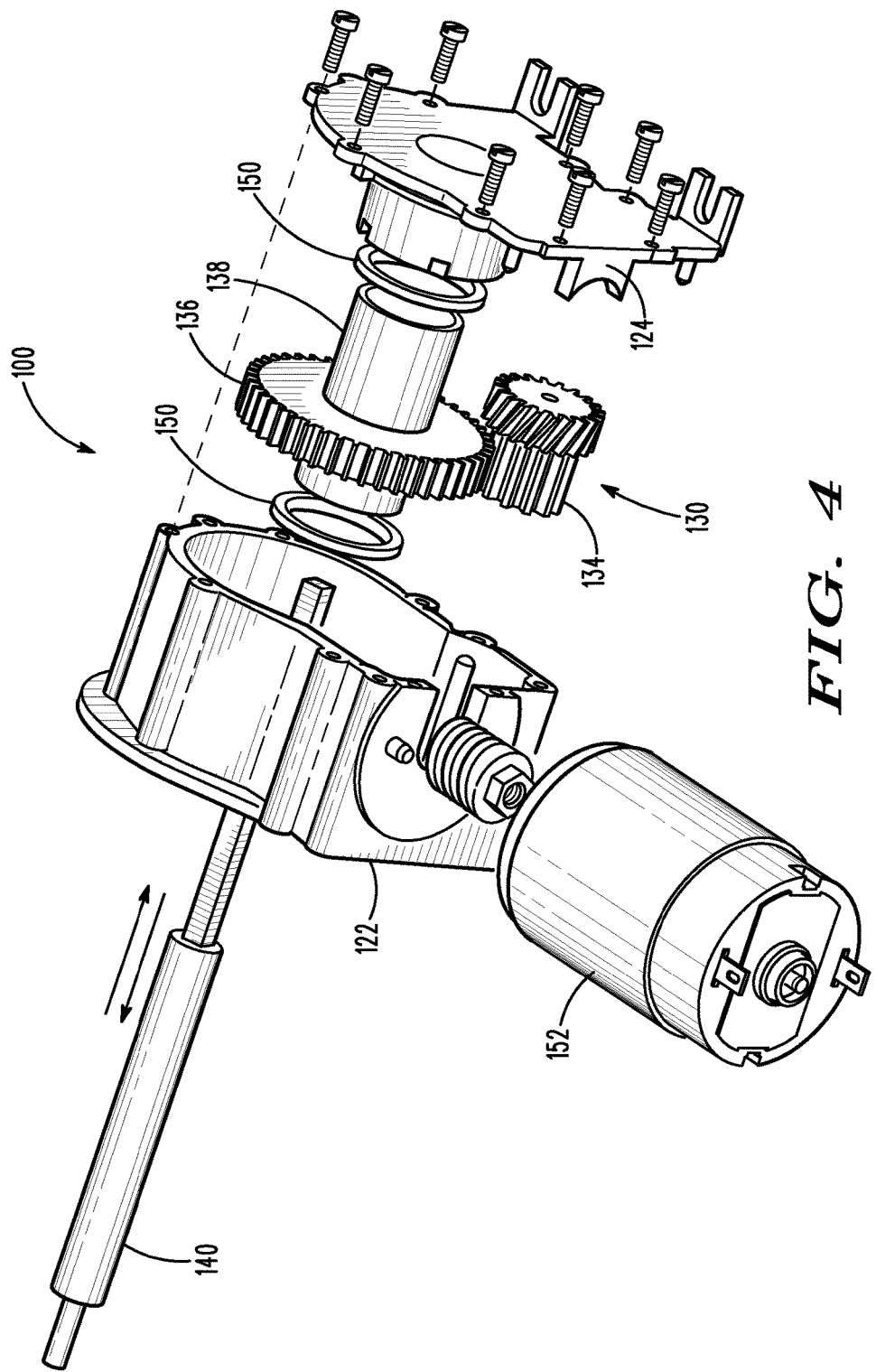
FIG. 4 is an exploded perspective view of another embodiment of the gear motor pump assembly; and, FIG. 5 is a perspective view of the gear motor pump assembly with a cylinder attached.
Figure 5:
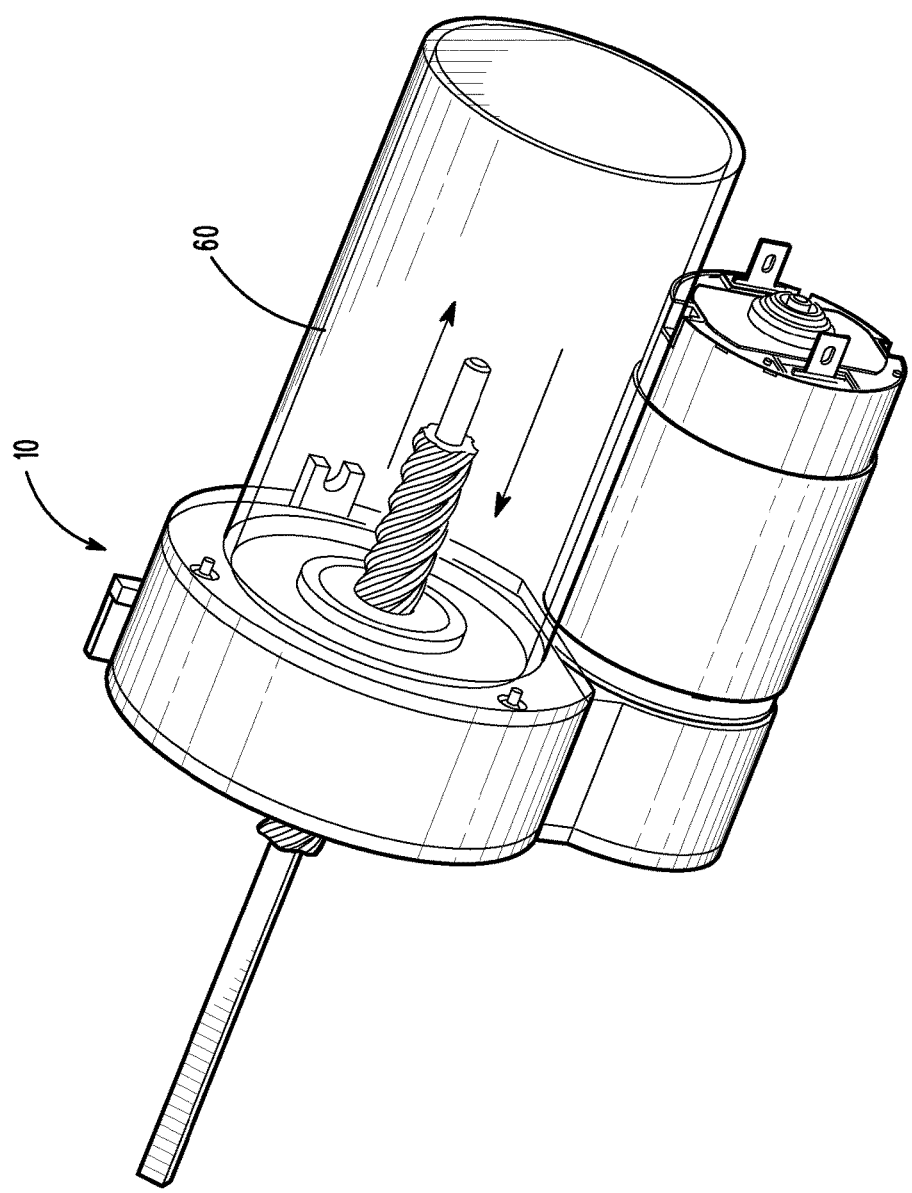

Referring to FIGS. 1-5, embodiments of the present gear motor pump assembly are illustrated. On example of a gear motor pump assembly 10 is shown in FIGS. 1-3. Another embodiment of a gear motor pump assembly 100 is shown in FIG. 4. FIG. 5 illustrates a gear motor pump assembly with a cylinder attached. The gear motor pump assemblies 10, 100 are used to drive a pump typically used in medical devices, including but not limited to, breast pumps.

FIG. 1 shows an exploded view of the first embodiment of the gear motor pump assembly 10. The assembly includes a housing 20 defining a gear chamber or a gearbox 22 and including a cover 24. A gear train 30 including a pinion gear 32, a first stage gear 34 and a last stage gear 36 are arranged and positioned within the gearbox. The assembly 10 further includes an output shaft 40 passing through and engaging with the last stage gear 36 of the gear train 30. The assembly also includes at least one spring 50 positioned between the last stage gear 36 and the gearbox 22 and/or the cover 24. Finally, a motor 52 having a motor shaft 54 extending axially therefrom is attached to the gearbox 22.

The housing 20 including its gear chamber or gearbox 22 and cover 24 are typically constructed from plastic, but may also be constructed from metal or other material suitable for use in devices requiring pumping action, including medical devices. The gearbox 22 and cover 24 may be attached together using any suitable fastener, including screws (shown in FIG. 4), or may also be connected through ultrasonic welding. Finally, the housing 20 can be any shape suitable for housing the gear train and for use in the particular device.

As shown in FIGS. 1 and 2, the gear train 30 includes a pinion 32, a first stage gear, which is a cluster gear 34, which includes a gear pin 35 and a last stage or output gear 36. The pinion gear 32 further connects to the motor 52 through the axial motor shaft 56. Each gear includes a plurality of teeth 32a, 34a, 36a, respectively, on its outer circumference, which interconnect or mesh with the teeth of the other respective gear. During operation, the outer teeth 32a of the pinion gear 32 mesh with and interconnect with the teeth 34a of the cluster gear 34. In turn, the teeth 34a of the cluster gear 34 mesh with the teeth 36a of the output gear 36. When the motor 52 is energized, the pinion gear 32 rotates which in turn rotates the cluster gear 34, which engages and rotates the output gear 36 and ultimately the output shaft 40 passing through the center of the output gear.

The output gear 36 includes a central hub 38, which houses an internal nut 38a (FIG. 3). The internal nut 38a is an acme threaded nut. Similarly, the output shaft 40 is an acme threaded screw, which is designed for engagement with the threaded internal nut 38a.

Referring to FIG. 3, a cut-away view of the gearbox 22 with the output gear 36 and the threaded output shaft 40 seated within the internal nut 38a, is shown. The threaded output shaft 40 passes through the central hub 38 of the output gear 36. The threads 42 of the output shaft 40 engage the internal nut 38a, which provides axial movement to the shaft as the output gear rotates. In this manner, the threaded output shaft 40 is moveable in a first forward direction A and in a second reverse direction B (depending on the motor stage), created by the opposing rotation of the output gear 36. The pumping action created by the rotational movement of the output gear 36, the nut 38a and the threaded shaft 40, drive a pumping mechanism of a device (not shown) within a cylinder 60, which is shown in parallel alignment with the motor (FIG. 5). However, it should be understood that the cylinder can be located in a different position, depending on the requirements of a particular device.

As noted, when the motor 52 is energized, the output gear 36 and internal nut 38a rotate causing the threaded output shaft 40 to travel in a first forward direction A a first distance, and reversing the motor rotation causes the shaft to travel in the opposite axial direction B, thus creating a pumping action. The first and second distance the threaded shaft 40 travels may vary depending on the degree of pumping action required; for example, the threaded shaft 40 may advance one inch and retract one inch. It should be understood that the distance of travel should not be limited, but may depend on the extent of pumping action required by a particular apparatus.

The present assembly 10 also includes at least one spring 50. The spring 50 is a compression spring, such as a helical compression spring or a wave spring, generally constructed from metal, including stainless steel, or carbon. The spring 50 may also be an O-ring, which is generally constructed from rubber or plastic. As shown in FIGS. 1, 2 and 4, the springs or compression springs 50 are positioned on opposing sides of the output gear 36 and specifically on either side of the central hub 38 of the output gear. Because of their location between the output gear 36 and the cover 24 of the housing and/or the gearbox 22, the compression springs 50 provide cushioning between all of these components, as well as, preventing the output gear from coming in contact with the gearbox 22 and the cover 24. Specifically, using two compression springs 50 on either side of the output gear central hub 38 purposefully eliminate contact between the output gear's surface from that of the gearbox and cover bearing journal during forward and reverse motions, which eliminates any knocking sound or noise associated with the output gear moving axially back and forth with the shaft. Use of the compression springs provides a desired feature of the present disclosure—quiet operation of the entire pump assembly.

The motor 52 is typically a direct current (DC) motor, such as a 6 volt DC motor. The motor 52 is capable of rotating in either a clockwise (first stage) or counterclockwise (second stage) direction. As the motor is energized, it activates the gear train assembly as discussed, thereby causing axial movement of the threaded output shaft 40 in opposing directions and through forward and reverse distances.

Referring to FIG. 5, there is shown another embodiment of the present gear motor pump assembly, referred to as 100. In this embodiment, the gear motor pump assembly 100 includes the same components as in the initial embodiment of the assembly 10, including a housing 120 defining a gear chamber or a gearbox 122 and cover 124, a gear train 130 having the central section 138 with the internal nut (not shown), the threaded output shaft 140 and the springs 150. The difference in this particular embodiment is that the motor 152 is arranged in perpendicular to the threaded output shaft 140. This embodiment illustrates that the assembly 10, 100 can be arranged to meet the specific requirements of a particular device.

In operation, the gear motor pump assembly 10, 100 of the present disclosure is useful in the operation of any pumping device, including medical pump devices. On such device benefitting from this gear motor assembly is a breast pump. A common complaint of individuals using breast pumps is that they are noisy. The quiet operation of the present gear motor pump assembly 10, 100 is advantageous for use in this application, as it provides a level of discretion when the pump is in use. Additionally, the quiet operation of the present gear motor pump assembly would be useful for implementation in a variety of medical pumping devices.

It should be noted that various changes and modifications to the presently preferred embodiments described herein will be apparent to those skilled in the art. Such changes and modifications may be made without departing from the spirit and scope of the present invention and without diminishing its attendant advantages.

Further, references throughout the specification to "the invention" are non-limiting, and it should be noted that claim limitations presented herein are not meant to describe the invention as a whole. Moreover, the invention illustratively disclosed herein suitably may be practiced in the absence of any element which is not specifically disclosed herein.

We claim:

1. A gear motor pump assembly comprising:
   a. a housing defining a gearbox and a cover;
   b. a motor having a motor shaft extending axially therefrom, the motor connected to the housing;
   c. a gear train positioned within the gearbox and connected to the motor, the gear train including an output gear having a central hub, the central hub of the output gear housing an internally threaded nut therethrough;
   d. an output shaft engaging with and moveable by the gear train, the output shaft passing through and meshing with the internally threaded nut of the output gear, the internally threaded nut providing axial movement to the output shaft as the output gear rotates;
   e. at least one compression spring disposed in direct contact with the central hub of the output gear and positioned between the output gear and one of the gearbox and the cover; and,
   wherein, when the motor is energized, the gear train rotates in a first direction, moving the output shaft a first distance, and wherein the gear train rotates in a second direction, opposite to the first direction, moving the output shaft a second distance opposite the first distance creating a pumping motion,
   wherein the at least one compression spring is configured to compress in response to axial movement of the output gear towards the one of the gearbox and the cover to thereby cushion the gear train.

2. The gear motor pump assembly of claim 1, wherein the gear train comprises: a pinion gear connected to the motor shaft; a first stage gear for engaging with the pinion gear; and, the output gear, said output gear movable through engagement with the first stage gear.

3. The gear motor pump assembly of claim 2, wherein the first stage gear is a cluster gear.

4. The gear motor pump assembly of claim 1, wherein the output shaft is an acme threaded screw.

5. The gear motor pump assembly of claim 1, wherein the internally threaded nut is an acme threaded nut.

6. The gear motor pump assembly of claim 1, wherein the assembly includes two compression springs.

7. The gear motor pump assembly of claim 6, wherein a first compression spring of the at least one compression spring is disposed between output gear and the housing cover and a second compression spring is disposed between the output gear and the gearbox.

8. The gear motor pump assembly of claim 7, wherein the compression springs are disposed one on either side of the central hub of the output gear.

9. The gear motor pump assembly of claim 1, wherein the compression spring includes a helical spring.

10. The gear motor pump assembly of claim 1, wherein the compression spring includes an O-ring.

11. The gear motor pump assembly of claim 6, wherein the two compression springs provide a cushion between the output gear and the housing cover and the output gear and the gearbox.

12. A gear motor pump assembly for use in a pumping device, the assembly comprising:
   a. a housing defining a gear chamber and including a base having a bottom wall portion and a sidewall portion extending from the bottom wall portion and a cover;
   b. a motor having a motor shaft extending axially therefrom, the motor connected to the housing;
   c. a gear train including an output gear having a central hub positioned within the gear chamber and connected to the motor, the central hub of the output gear housing an internally threaded nut therethrough;
   d. an output shaft engaging with and moveable by the gear train, the output shaft passing through and meshing with the internally threaded nut of the output gear, the internally threaded nut providing axial movement to the output shaft as the output gear rotates;
   e. at least one compression spring disposed entirely within the gear chamber of the housing in direct contact with the central hub of the output gear and positioned between the output gear and one of the bottom wall portion and the cover,
   wherein the spring absorbs concussion between the output gear and the one of the bottom wall portion and the cover as the output shaft moves back and forth axially through the internally threaded nut of the output gear by compressing due to axial movement of the output gear, and wherein, when the motor is energized in a first direction, the gear train rotates in a first direction moving the output shaft a first distance, and wherein when the motor is energized in a second direction, the gear train rotates in a second direction opposite to the first direction moving the output shaft a second distance opposite the first distance, wherein the movement of the output shaft between the first distance and the second distance creates a pumping motion.

* * * * *